US012653579B2

(12) United States Patent
Montello et al.

(10) Patent No.: US 12,653,579 B2
(45) Date of Patent: Jun. 16, 2026

(54) ALERT PROCESSOR FOR A BONE FIXATION DEVICE

(71) Applicant: Synthes GmbH, Oberdorf (CH)

(72) Inventors: Albert A. Montello, West Chester, PA (US); Scott P. Lavoritano, West Chester, PA (US); Oren Cohen, Moreshet (IL); Shahar Harari, Tel-Aviv (IL); Dror Albo, Givat-Ada (IL)

(73) Assignee: Synthes GmbH, Oberdorf (CH)

( * ) Notice: Subject to any disclaimer, the term of this patent is extended or adjusted under 35 U.S.C. 154(b) by 0 days.

(21) Appl. No.: 18/640,526

(22) Filed: Apr. 19, 2024

(65) Prior Publication Data

US 2024/0350172 A1      Oct. 24, 2024

Related U.S. Application Data

(60) Provisional application No. 63/461,031, filed on Apr. 21, 2023.

(51) Int. Cl.
*A61B 17/66*          (2006.01)
*A61B 17/64*          (2006.01)
(Continued)

(52) U.S. Cl.
CPC .......... *A61B 17/66* (2013.01); *A61B 17/6441* (2013.01); *A61B 2017/00039* (2013.01);
(Continued)

(58) Field of Classification Search
CPC ......... A61B 17/62; A61B 17/64; A61B 17/66; A61B 17/6441; A61B 34/10; G16H 40/40; G16H 40/63; G16H 20/30; G16H 50/20
See application file for complete search history.

(56) References Cited

U.S. PATENT DOCUMENTS 4,889,111 A      12/1989  Ben-dov
4,973,331 A      11/1990  Pursley et al.
(Continued)

FOREIGN PATENT DOCUMENTS

AU          2013382253 B2      11/2019
AU          2020354546 A1      3/2022
(Continued)

OTHER PUBLICATIONS

Seide, K., et al., "Medical Robotics and Computer Assisted Surgery", 2004, pp. 64-69.
(Continued)

*Primary Examiner* — Christopher J Beccia
(74) *Attorney, Agent, or Firm* — Flaster Greenberg PC

(57)          ABSTRACT
An adjustable bone fixation device for moving a bone includes at least two strut units, at least one meter and a system controller. Each strut unit includes a motor to move a strut. The meter measures a signal generated by the motor during the movement of its strut. The signal is useful in determining a torque or a current of the motor. The system controller activates at least two of the motors and uses the determined torque or the determined current to identify if there is a clinical situation of the bone or a system issue and provides an alert accordingly.

23 Claims, 10 Drawing Sheets

(51) Int. Cl.
　　　*A61B 17/00*　　　　(2006.01)
　　　*A61B 90/00*　　　　(2016.01)
(52) U.S. Cl.
　　　CPC .............. *A61B 2017/00075* (2013.01); *A61B 2017/00119* (2013.01); *A61B 2017/00398* (2013.01); *A61B 2090/066* (2016.02)

(56) References Cited

U.S. PATENT DOCUMENTS

| | | | |
|---|---|---|---|
| 5,108,394 A | 4/1992 | Kurokawa et al. | |
| 5,180,380 A | 1/1993 | Pursley et al. | |
| 5,339,533 A | 8/1994 | Richardson | |
| 5,358,504 A | 10/1994 | Paley et al. | |
| 5,437,668 A | 8/1995 | Aronson et al. | |
| 5,728,095 A | 3/1998 | Taylor et al. | |
| 5,766,173 A | 6/1998 | Ross et al. | |
| 7,306,601 B2 | 12/2007 | McGrath et al. | |
| 8,157,800 B2 | 4/2012 | Vvedensky et al. | |
| 8,202,273 B2 | 6/2012 | Karidis | |
| 8,282,652 B2 | 10/2012 | Mackenzi et al. | |
| 8,333,766 B2 | 12/2012 | Edelhauser et al. | |
| 8,491,660 B2 | 7/2013 | Kaiser et al. | |
| 8,515,538 B1 | 8/2013 | Osorio et al. | |
| 8,574,232 B1 | 11/2013 | Ross et al. | |
| 8,585,703 B2 | 11/2013 | Verma et al. | |
| 8,702,705 B2 | 4/2014 | Ziran et al. | |
| 8,864,750 B2 | 10/2014 | Ross et al. | |
| 8,864,763 B2 | 10/2014 | Murray et al. | |
| 8,915,915 B2 | 12/2014 | Harrison et al. | |
| 9,155,559 B2 | 10/2015 | Ross et al. | |
| 9,186,180 B2 | 11/2015 | Chang et al. | |
| 9,204,937 B2 | 12/2015 | Edelhauser et al. | |
| 9,289,238 B2 | 3/2016 | Ross et al. | |
| 9,524,581 B2 | 12/2016 | Haskell | |
| 9,526,523 B2 | 12/2016 | Aoki et al. | |
| 9,610,102 B2 | 4/2017 | Singh | |
| 9,681,892 B2 | 6/2017 | Ross et al. | |
| 9,717,528 B2 | 8/2017 | Singh | |
| 9,788,861 B2 | 10/2017 | Murray et al. | |
| 9,895,502 B2 | 2/2018 | Hatanaka | |
| 9,918,742 B2 | 3/2018 | Wilhelm et al. | |
| 9,949,758 B2 | 4/2018 | Vikinsky et al. | |
| 10,010,350 B2 | 7/2018 | Mannanal et al. | |
| 10,064,664 B2 | 9/2018 | Forsell | |
| 10,080,586 B2 | 9/2018 | Ross et al. | |
| 10,082,384 B1 | 9/2018 | Singh | |
| 10,154,884 B2 | 12/2018 | Kumar et al. | |
| 10,194,944 B2 | 2/2019 | Edelhauser et al. | |
| 10,390,859 B2 | 8/2019 | Sakkers et al. | |
| 10,492,832 B2 | 12/2019 | Singh | |
| 10,631,897 B2 | 4/2020 | Park et al. | |
| 10,881,433 B2 | 1/2021 | Edelhauser et al. | |
| 10,898,229 B2 | 1/2021 | Park et al. | |
| 10,932,713 B2 | 3/2021 | Lewis et al. | |
| 10,945,765 B2 | 3/2021 | Miller | |
| 10,962,166 B1 | 3/2021 | Liu | |
| 11,076,801 B2 | 8/2021 | Cohen et al. | |
| 11,083,497 B2 | 8/2021 | Mannanal et al. | |
| 11,206,981 B2 | 12/2021 | Chin | |
| 11,207,103 B2 | 12/2021 | Singh | |
| 11,259,874 B1 | 3/2022 | Landon et al. | |
| 11,266,444 B2 | 3/2022 | Chen | |
| 11,304,757 B2 | 4/2022 | Gutmann et al. | |
| 11,376,054 B2 | 7/2022 | Kemper et al. | |
| 11,395,679 B2 | 7/2022 | Noblett et al. | |
| 11,439,436 B2 | 9/2022 | Gutmann et al. | |
| 11,471,192 B2 | 10/2022 | Mullaney | |
| 11,600,368 B2 | 3/2023 | Austin et al. | |
| 2006/0276786 A1 | 12/2006 | Brinker | |
| 2007/0055233 A1 | 3/2007 | Brinker | |
| 2008/0139978 A1 | 6/2008 | Talish et al. | |
| 2008/0234554 A1 | 9/2008 | Vvedensky et al. | |
| 2010/0087819 A1 | 4/2010 | Mullaney | |
| 2013/0041288 A1 | 2/2013 | Taylor et al. | |
| 2013/0131675 A1 | 5/2013 | Vasta et al. | |

| | | | |
|---|---|---|---|
| 2013/0245625 A1 | 9/2013 | Vasta et al. | |
| 2016/0374561 A1 | 12/2016 | Buescher et al. | |
| 2017/0071632 A1* | 3/2017 | Vikinsky ................ A61B 17/62 | |
| 2017/0181800 A1 | 6/2017 | Nikonovas | |
| 2019/0277373 A1 | 9/2019 | Matsuto et al. | |
| 2019/0282276 A1 | 9/2019 | Burgherr et al. | |
| 2019/0336171 A1 | 11/2019 | Lavi et al. | |
| 2020/0253640 A1 | 8/2020 | Mullaney | |
| 2020/0352623 A1 | 11/2020 | Stickel et al. | |
| 2020/0357501 A1 | 11/2020 | Austin et al. | |
| 2020/0390471 A1 | 12/2020 | Mannanal et al. | |
| 2021/0027879 A1 | 1/2021 | Noblett et al. | |
| 2021/0038147 A1 | 2/2021 | Cohen et al. | |
| 2021/0077149 A1 | 3/2021 | Edelhauser et al. | |
| 2021/0153944 A1 | 5/2021 | Nikonovas | |
| 2021/0346059 A1 | 11/2021 | Singh et al. | |
| 2021/0361322 A1 | 11/2021 | Sun et al. | |
| 2021/0401465 A1 | 12/2021 | Singh et al. | |
| 2022/0022963 A1 | 1/2022 | Yu et al. | |
| 2022/0071662 A1 | 3/2022 | Heotis et al. | |
| 2022/0093228 A1 | 3/2022 | Austin et al. | |
| 2022/0237797 A1 | 7/2022 | Gutmann et al. | |
| 2022/0273341 A1 | 9/2022 | Lavi et al. | |
| 2022/0354539 A1* | 11/2022 | Ferrante ................ A61B 90/14 | |
| 2022/0361921 A1 | 11/2022 | Burgherr et al. | |
| 2022/0378476 A1 | 12/2022 | Gutmann et al. | |
| 2023/0000524 A1 | 1/2023 | Qi et al. | |
| 2023/0023669 A1 | 1/2023 | Noblett et al. | |
| 2023/0086184 A1 | 3/2023 | Noblett et al. | |
| 2023/0090626 A1 | 3/2023 | Noblett et al. | |
| 2023/0233232 A1 | 7/2023 | Roberts et al. | |
| 2023/0255665 A1 | 8/2023 | Pak et al. | |

FOREIGN PATENT DOCUMENTS

| | | | |
|---|---|---|---|
| AU | 2021228690 A1 | 9/2022 | |
| CA | 2267232 C | 9/2009 | |
| DE | 102015121355 A1 | 6/2017 | |
| DE | 102015121357 A1 | 6/2017 | |
| EP | 0386912 B1 | 8/1995 | |
| EP | 2152177 B1 | 4/2011 | |
| EP | 2723259 A1 | 4/2014 | |
| EP | 2117635 B1 | 12/2015 | |
| EP | 2405834 B1 | 7/2016 | |
| EP | 2767252 B1 | 4/2019 | |
| EP | 3245966 B1 | 6/2020 | |
| EP | 3776568 A1 | 2/2021 | |
| EP | 3917419 A1 | 12/2021 | |
| EP | 3503830 B1 | 5/2022 | |
| EP | 4000545 A1 | 5/2022 | |
| EP | 4034009 A1 | 8/2022 | |
| EP | 4087513 A1 | 11/2022 | |
| EP | 4110219 A1 | 1/2023 | |
| EP | 4135606 A1 | 2/2023 | |
| EP | 4192374 A1 | 6/2023 | |
| EP | 4197463 A1 | 6/2023 | |
| EP | 4226878 A1 | 8/2023 | |
| JP | 5830118 B2 | 10/2015 | |
| JP | 2019197569 A | 11/2019 | |
| KR | 101809291 B1 | 12/2017 | |
| KR | 102467617 B1 | 11/2022 | |
| WO | WO 9535061 A2 | 12/1995 | |
| WO | WO 2010042619 A1 | 4/2010 | |
| WO | WO 2010042619 A4 | 6/2010 | |
| WO | WO 2011026475 A1 | 3/2011 | |
| WO | WO 2011163406 A2 | 12/2011 | |
| WO | WO 2012102685 A1 | 8/2012 | |
| WO | WO 2013172800 A1 | 11/2013 | |
| WO | WO 2014163591 A1 | 10/2014 | |
| WO | WO 2015142298 A3 | 11/2015 | |
| WO | WO 2016159901 A1 | 10/2016 | |
| WO | WO 2017150782 A1 | 9/2017 | |
| WO | 2019195231 A1 | 10/2019 | |
| WO | WO 2019237513 A2 | 12/2019 | |
| WO | WO 2020029378 A1 | 2/2020 | |
| WO | 2020092049 A1 | 5/2020 | |
| WO | WO 2021069078 A1 | 4/2021 | |
| WO | WO 2021122701 A1 | 6/2021 | |
| WO | WO 2021142213 A1 | 7/2021 | |

(56)          References Cited

FOREIGN PATENT DOCUMENTS

| WO | WO 2021173931 A1 | 9/2021 |
|----|----|----|
| WO | WO 2021221920 A1 | 11/2021 |
| WO | WO 2022024133 A1 | 2/2022 |
| WO | WO 2022031891 A1 | 2/2022 |
| WO | WO 2022112274 A1 | 6/2022 |
| WO | WO 2022144684 A1 | 7/2022 |
| WO | WO 2022204096 A1 | 9/2022 |
| WO | WO 2023048948 A1 | 3/2023 |
| WO | 2023163874 A1 | 8/2023 |
| WO | 2023205046 A1 | 10/2023 |
| WO | 2023230203 A1 | 11/2023 |
| WO | 2023244586 A1 | 12/2023 |
| WO | 2024059116 A1 | 3/2024 |
| WO | 2024102351 A1 | 5/2024 |
| WO | 2024102395 A1 | 5/2024 |

OTHER PUBLICATIONS

McBride, A., et al., "The programmable hexapod: historical perspective, theoretical basis and relevance to orthopaedic practice; Bone & Joint360", Aug. 2015, vol. 4, Issue 4, 4 pages.

Wendlandt, R, et al., "ECIFMBE 2008, IFMBE Proceedings 22", 2008, Hamburg, Germany, pp. 1679-1682.

Bright et al., "Preliminary experience with motorized distraction for tibial lengthening; Burghardt RD: Strat Traum Limb Recon 2014", Mar. 2014, 5 pages.

"Maxframe AUTOSTRUTTm Multi-Axial Correction System Patient User Manual", DePuySynthes, 2023, 10 pages.

"Maxframe Autostrut™ Multi-Axial Correction System", DePuySynthes, 2022, 2023, 4 pages.

Me, Müller , et al., "Maxframe Autostrut™ Multi-Axial Correction System Surgical Technique", DePuySynthes, 2023, 64 pages.

* cited by examiner

ALERT PROCESSOR FOR A BONE FIXATION DEVICE

CROSS-REFERENCE TO RELATED APPLICATIONS

This application claims the benefit of Provisional U.S. Patent Application No. 63/461,031, filed Apr. 21, 2023, the entire disclosure of which is hereby incorporated by reference herein in its entirety.

BACKGROUND

External bone fixation devices are known in the art and are used to lengthen bones and for correcting bone deformities. FIG. 1, to which reference is now made, shows an example device 10 with six struts 12 connecting two rings 14 to adjust the relative positioning of the two parts of a broken bone 16. In some devices, struts 12 are connected vertically, though in FIG. 1 they are connected at angles. Each of the struts 12 may be formed of a telescoping rod with an external thread 13 about which a bolt mechanism may move, thereby extending the respective strut 12.

Struts 12 typically have several sizes, such as small, medium, and large. The surgeon affixing the bone fixation device selects the strut size according to the initial distance between the rings 14 and typically expects to swap to a longer strut at some point during the treatment.

US20080234554 to Vvedensky et al. teaches a motorized version where each strut of the fixation device is individually activatable and U.S. Pat. No. 11,076,801 to Cohen et al. teaches a device with control circuitry which receives a treatment plan and measures a change in the distance between the two rings.

The MaxFrame AutoStrut, commercially available from DePuy Synthes of the United States, is an automated, motorized and adjustable bone fixation device which automatically moves the struts according to a treatment plan, such as moving 1 mm/day in multiple (e.g., 1-20) steps per day. As shown in FIGS. 2A and 2B, to which reference is now made, the bone fixation device, labeled 100, has a motor 110 per strut 106 that is controlled by a control unit 101 and that changes strut length according to a pre-defined treatment plan.

Control unit 101 is mounted on a front end of the bone fixation device 100, such as on the upper ring 14. Control unit 101 has a panel which includes one or more visual indicators and is oriented or tilted to face the eyes of the patient. Control unit 101 is connected to each strut unit 102 via its motor 110. Each strut unit 102 is connected to the control unit 101, directly or via a strut assembly connector 248 or 258, both of which transmit power and data between the strut unit 102 and the control unit 101.

The control unit 101 comprises a controller 104 (e.g., as shown in FIG. 2B), connected to a memory 268, which stores treatment protocols, values of at least one treatment parameter, log files of the control unit, indications regarding the activation of each of the motors connected to the control unit, and indications regarding the current length of each of the struts. The treatment parameter comprises for example an activation parameter of each of the motors, for example activation timing, number of strut extension sessions per hour, per day, per week and/or per month, strut extension length per session, and/or motor activation parameters needed for each strut extension session.

The control unit 101 comprises a user interface 264 which delivers a human detectable indication, for example a visual indication and/or an audio indication to the patient, to a physician, to a nurse or to a caregiver of the patient. In some embodiments, the controller 104 is configured to monitor the proper connection of the motors to the motor adaptors and/or the proper activation of the motors, by measuring the electrical current of the motors. Also, if values of at least one electrical parameter of a motor is different from a predetermined value or a range of predetermined values, the control system stops the operation of the motor and/or delivers an alert signal.

The control unit 101 also comprises a communication circuitry 270, configured to transmit and receive signals from a remote device, which can be a cellular phone, a wearable device, a remote computer, a tablet, a remote server, an information storage cloud. Communication circuitry 270 transmits and receives wireless signals. If the information received from the motors or from the motor adaptors indicates that a motor is not connected properly, or that a treatment plan progress is not as desired, the controller 104 signals the communication circuitry to deliver an indication to a remote device, for example to signal the remote device to generate a human detectable indication.

SUMMARY

There is therefore provided, in accordance with a preferred embodiment of the present disclosure, an adjustable bone fixation device for moving a bone. The device includes at least two strut units, at least one meter, a system controller and an alert processor. Each strut unit includes a motor to move a strut. Each meter measures a signal generated by the motor during a movement of its strut. The signal is useful in determining a torque or a current of the motor. The system controller activates at least two of the motors and determines the torque or the current of at least two of the motors. The alert processor identifies if the determined torque or the determined current indicates a clinical situation of the bone or a system issue and provides an alert accordingly.

Moreover, in accordance with a preferred embodiment of the present disclosure, the motor is a brushed motor and the at least one meter is a current meter.

Alternatively, in accordance with a preferred embodiment of the present disclosure, the motor is a brushless motor and the at least one meter is a voltmeter and a rotational speedometer.

Further, in accordance with a preferred embodiment of the present disclosure, the alert processor identifies a problem when at least one parameter of the determined torque or the determined current is out of a predetermined range for the at least one parameter.

Still further, in accordance with a preferred embodiment of the present disclosure, the alert processor determines that a single strut unit of the at least two strut units has a problem if a motor of the single strut unit has an out-of-range value for a parameter of the determined torque or the determined current. An out-of-range value for a parameter may be a value that is outside of the predetermined range for the parameter.

Moreover, in accordance with a preferred embodiment of the present disclosure, the alert processor determines the clinical situation if a majority of the motors have an out-of-range value for a parameter of their respective determined torques or determined currents.

Further, in accordance with a preferred embodiment of the present disclosure, the alert processor determines that a single strut unit has a problem if a motor of the single strut unit has a sudden jump in a value for a parameter of the determined torque or the determined current. A sudden jump in a value for a parameter may be defined as a change (e.g., an abrupt change) in the parameter over a predetermined period of time that is greater than a predetermined amount.

Still further, in accordance with a preferred embodiment of the present disclosure, if the alert processor classifies the problem as an end of travel problem, the alert processor instructs the system controller to compare a current axial location of the single strut unit with a predefined travel limit for the single strut unit.

Moreover, in accordance with a preferred embodiment of the present disclosure, the alert processor determines if a strut swap was not done (e.g., performed) or was forgotten and provides an appropriate alert.

Further, in accordance with a preferred embodiment of the present disclosure, the alert processor determines that a single strut unit has a problem if the motor of the single strut unit has a continuous elevation of a value for a parameter of the determined torque or the determined current during a treatment period.

Still further, in accordance with a preferred embodiment of the present disclosure, the alert processor identifies the clinical situation if a majority of the motors have a continuous elevation of a value for a parameter of the determined torques or determined currents during a treatment period.

There is also provided, in accordance with a preferred embodiment of the present disclosure, a method for an adjustable bone fixation device for moving a bone, the device having at least two strut units, and each strut unit including a motor to move a strut. The method includes activating at least two of the motors, measuring signals generated by at least two activated motors, the signals being useful in determining torques or currents of the at least two of the motors, and identifying if the determined torques or determined currents indicate a clinical situation of the bone or a system issue and alerting accordingly.

Moreover, in accordance with a preferred embodiment of the present disclosure, the at least two activated motors are brushed motors and the signals are current signals.

Alternatively, in accordance with a preferred embodiment of the present disclosure, the at least two activated motors are brushless motors, and wherein the signals are voltage signals or rotational speed signals.

Further, in accordance with a preferred embodiment of the present disclosure, the step of identifying includes reviewing the determined torque or the determined current to determine when at least one parameter of the determined torque or determined current is out of a predetermined range for the at least one parameter.

Still further, in accordance with a preferred embodiment of the present disclosure, the step of identifying includes determining that a single strut unit of the at least two strut units has a problem if a motor of the single strut unit has an out-of-range value for a parameter of the determined torque or the determined current.

Moreover, in accordance with a preferred embodiment of the present disclosure, the step of identifying includes determining the clinical situation if a majority of the motors have an out-of-range value for a parameter of their determined torques or determined currents.

Further, in accordance with a preferred embodiment of the present disclosure, the step of identifying includes determining that a single strut unit has a problem if a motor of the single strut unit has a sudden jump in a value for a parameter of the determined torque. A sudden jump in the value for the parameter of the determined torque or determined current may be defined as a change (e.g., an abrupt change) in the determined torque or determined current over a predetermined period of time that is greater than a predetermined torque amount or a predetermined current amount, respectively.

Still further, in accordance with a preferred embodiment of the present disclosure, if the step of identifying includes classifies the problem as an end of travel problem, comparing a current axial location of the single strut unit with a predefined travel limit for the single strut unit.

Moreover, in accordance with a preferred embodiment of the present disclosure, the step of identifying includes determining if a strut swap was not done (e.g., performed) or was forgotten and providing an appropriate alert.

Further, in accordance with a preferred embodiment of the present disclosure, the step of identifying includes determining that a single strut unit has a problem if the motor of the single strut unit has a continuous elevation of a value for a parameter of the determined torque or the determined current during a treatment period.

Still further, in accordance with a preferred embodiment of the present disclosure, the step of identifying includes identifying the clinical situation if a majority of the motors have a continuous elevation of a value for a parameter of the determined torques or the determined currents during a treatment period.

Moreover, in accordance with a preferred embodiment of the present disclosure, the alert processor is located remotely to the device.

Further, in accordance with a preferred embodiment of the present disclosure, the system controller includes communication circuitry to communicate to an external device which communicates with the alert processor.

Finally, in accordance with a preferred embodiment of the present disclosure, the external device is a smartphone of a patient or a caregiver.

DETAILED DESCRIPTION

Figure 1:
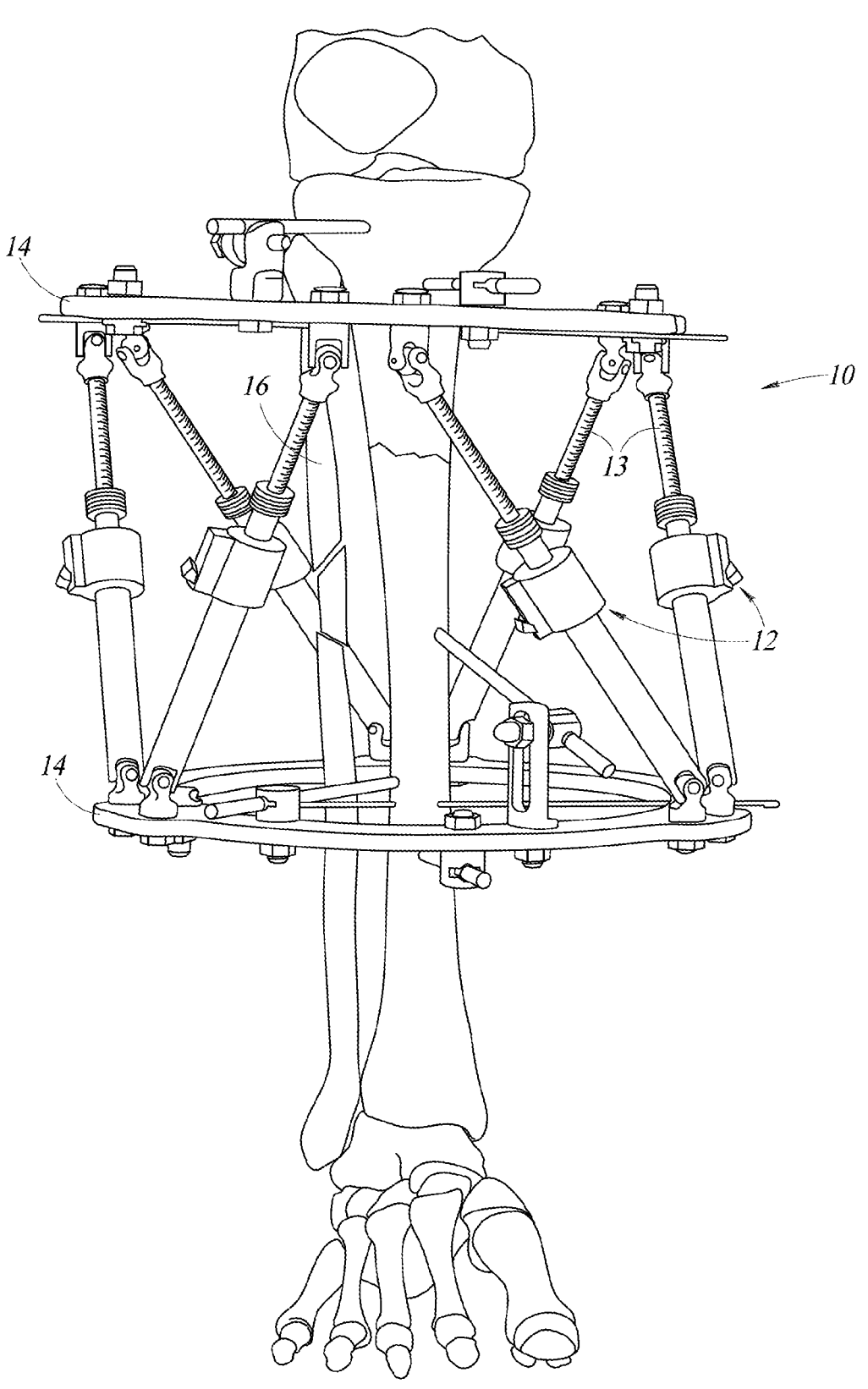
FIG. 1 is a schematic illustration of an exemplary external bone fixation device.

The present disclosure relates to adjustable bone fixation devices generally, to automatic adjustable bone fixation devices in particular and to methods for adjustable bone fixation devices. In the following detailed description, numerous specific details are set forth in order to provide a thorough understanding of the invention. However, it will be understood by those skilled in the art that the present disclosure may be practiced without these specific details. In other instances, well-known methods, procedures, and components have not been described in detail so as not to obscure the present disclosure. It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

It can be appreciated that there are many ways that a motorized bone fixation device could fail during treatment (e.g., not move properly when the motors are activated). For example, it may fail due to clinical situations, which are typically that the bone consolidation is not as expected and/or that soft tissue movement consumes a high force. In another example, it may fail due to system issues, such as that something is in the way of one or more struts (e.g., maybe the strut has dirt in it, or is stuck on a sheet, a couch, a pantleg, etc.) or that one or more of its struts have reached an end of its travel (e.g., is fully extended).

It can be appreciated that one indicator of pending failure is the amount of axial force generated by the motor(s) which move the struts of a motorized adjustable fixation device. When the force is out of a predefined range, there is something which is keeping the strut from moving properly. The challenge is to identify problematic situations that might cause the treatment to stop (or slow down) and to understand the nature of the problem (e.g., clinical issue or system issue).

It can be appreciated that the axial force may be measured in a motorized adjustable fixation device by checking the current of the strut motor(s). In a brushed DC motor, for example, the current is correlated to motor torque, and the motor torque is correlated to the axial load generated when the strut is moving. The current may be measured on each motor separately or in a single location if the motors are not activated simultaneously.

Figure 3:
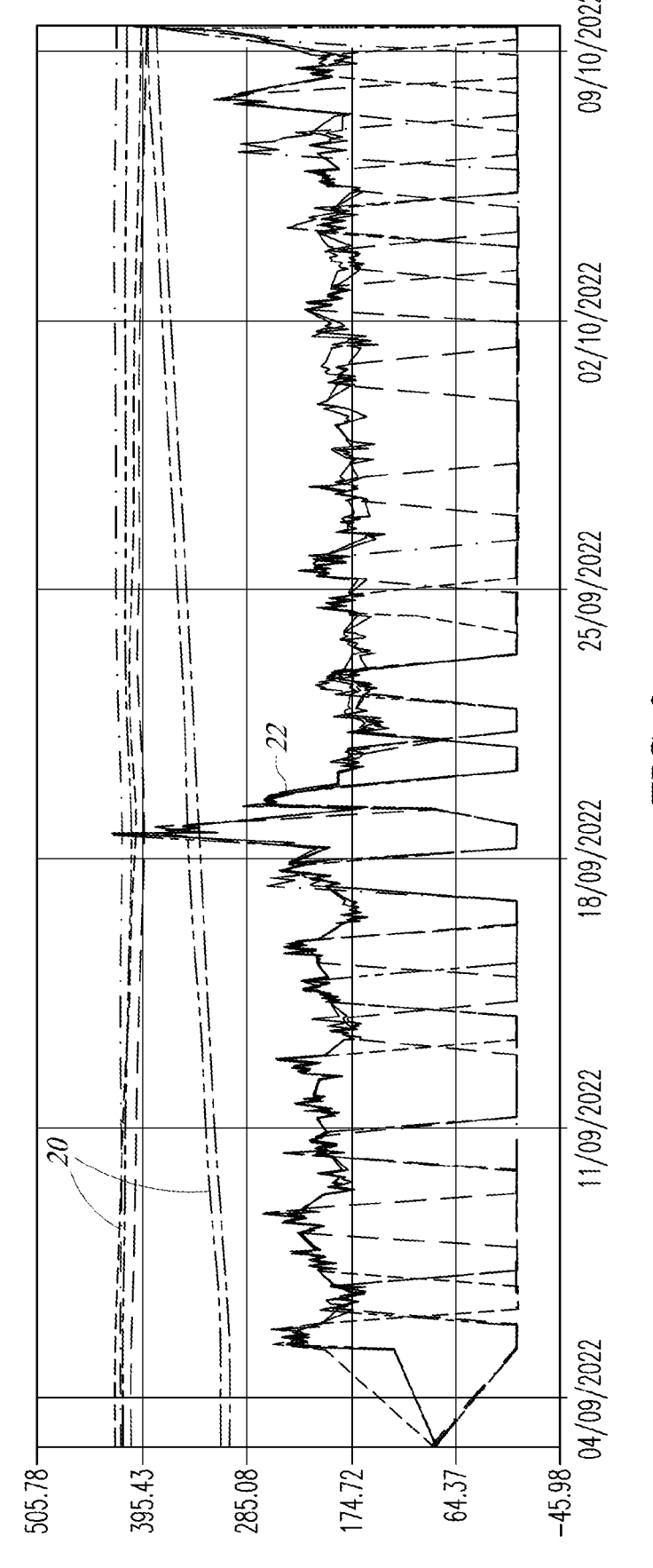
FIG. 3 is a graphical illustration showing typical extension over time of each of 6 struts of the device of FIG. 1.

Reference is now made to FIG. 3, which illustrates an exemplary treatment taking place between a treatment start date and a treatment end date. As shown by the graph, the exemplary start date is 4 Sep. 2022, and the exemplary end date is 9 October. FIG. 3 illustrates multiple graphs 20 showing typical extension (in millimeters) over time of each of 6 struts, each one marked with a different symbol. Note that the struts in this example operate multiple times each day, though typically not at night, and that each strut has a slightly different trajectory as defined by the surgeon. The surgeon typically defines a different treatment plan for each patient.

FIG. 3 also shows graphs 22 of the current, in mA, applied to each motor 110 as measured by current meters of the struts. The current starts and stops, according to the activation timing of the motors 110. When the motors 110 are active, the measured current generally fluctuates within a predefined level. For example, the predefined level is between 170 and 286 mA. An example of this predefined, or acceptable current, level can be seen on graphs 22 of FIG. 3 during the first 10 days of the treatment up to, for example, 18 Sep. 2022. However, FIG. 3 shows that sometime on, for example, 19 Sep. 2022, the sensed current for a number of the struts peaked above 400 mA. The problem was fixed and the sensed current went back down to its normal levels until, for example, 9 Oct. 2022 when the currents jumped again to high values.

Figure 4A:
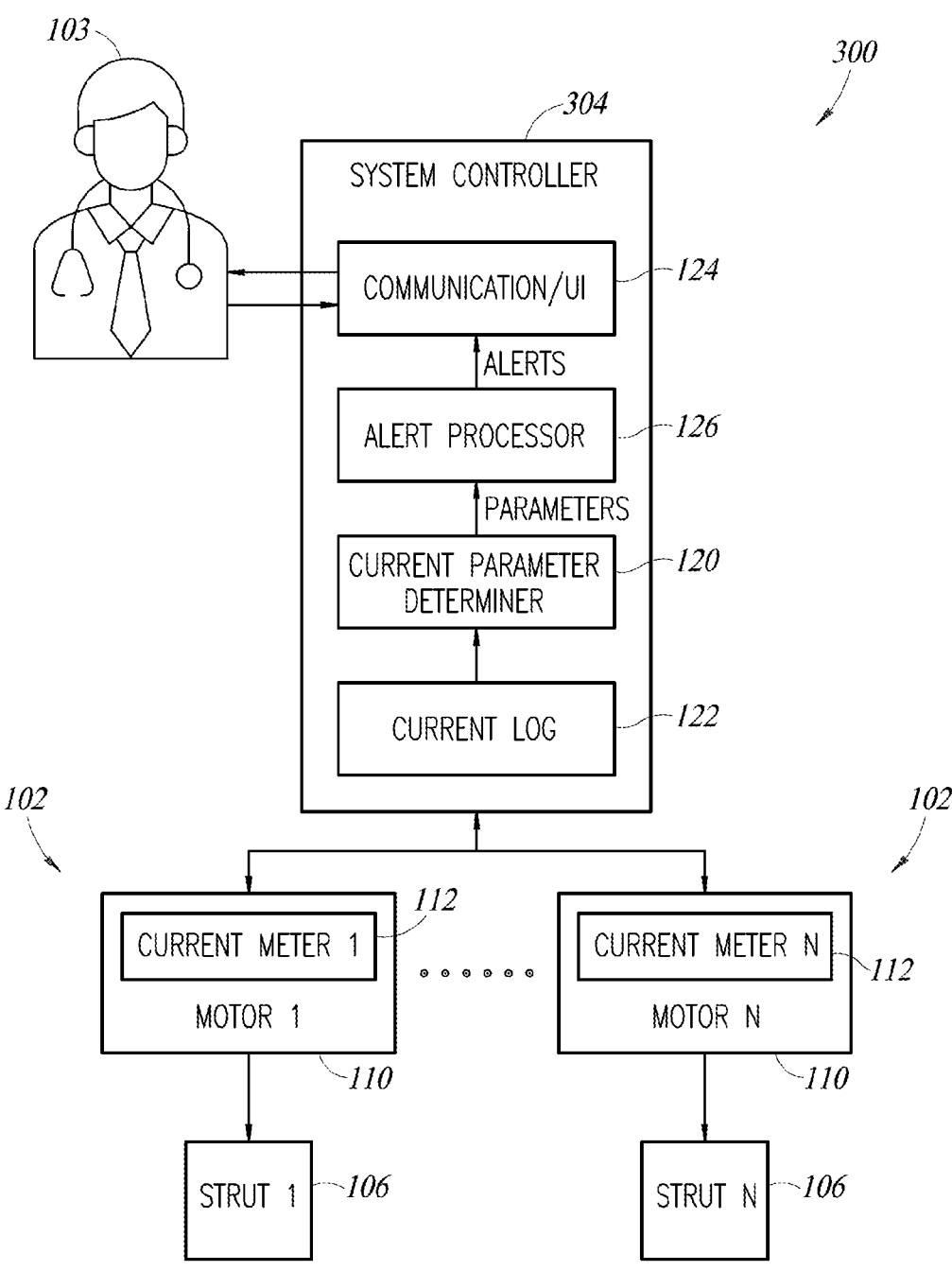
FIGS. 4A and 4B are schematic illustrations of two embodiments of an alert system for an automated, motorized bone fixation device, constructed and operative in accordance with a preferred embodiment of the present disclosure.

Reference is now made to FIG. 4A, which illustrates an automated, the motorized bone fixation device 300 having an alert processor 126, constructed and operative in accordance with an embodiment of the present disclosure. Device 300 comprises at least two strut units 102 and a system controller 304.

Each strut unit 102 may comprise a strut 106 and a motor 110 (e.g., an electric motor). System controller 304 may control the operation of strut units 102 according to a treatment plan of a physician 103, by starting and stopping the relevant electric motor 110 associated with the relevant strut 106, thereby moving the relevant strut 106.

In the embodiment of FIG. 4A, each electric motor 110 may be connected to a current meter 112 which may measure the current of its motor 110. As discussed hereinabove with respect to FIG. 3, the current sensed by current meter 112 may indicate an issue with one or more electric motor 110 or that one or more of the struts 106 may not be operating properly.

In the embodiment of FIG. 4A, system controller 304 may comprise a current log 122, in which each current meter 112 may store the current values it has sensed, a current parameter determiner 120, an alert processor 126 and a communication unit 124. Current parameter determiner 120 may determine various parameters of the current, such as the average current (e.g., for a given period of time), the peak current, change in the average current etc., and alert processor 126 may generate alerts if any of these values, or a combination of these values, or a combination of these values with those of another sensor, are outside of a predefined range, such as the predefined range discussed above with reference to FIG. 3. Current parameter determiner 120 may also regularly report on the activations of strut units 102 to physician 103 and may transmit alerts as they occur.

For example, current parameter determiner 120 may measure an average of each motor's absolute current along the course of the treatment and may store this information in current log 122. Alert processor 126 may check if the average current is a predefined percentage above its 'normal', where the percentage may be predefined or customizable and may typically be from 20-30%, 30-75%, or more than 75%, if desired.

Other parameters which current parameter determiner 120 may determine include the relative current change along the treatment for each motor and any sudden peak current of a specific motor, where a peak current may be defined as desired, such as being 20% above a normal current for a very short time, such as 0.02-0.5 seconds, or as being any other percentage, such as more than 75% above the normal current.

It can be appreciated that a measurement system formed of current parameter determiner 120, alert processor 126 and current meters 112 may identify a problem in the making and may provide an early warning to the caregiver or physician before the fixation device stops treatment entirely. Alternatively, or in addition, the measurement system may provide an understanding of the nature of a problem for an efficient repair. This early warning may enable the caregiver or physician to better adjust the treatment plan for a specific patient or to check or provide guidance to the patient on system related issues.

Figure 4B:
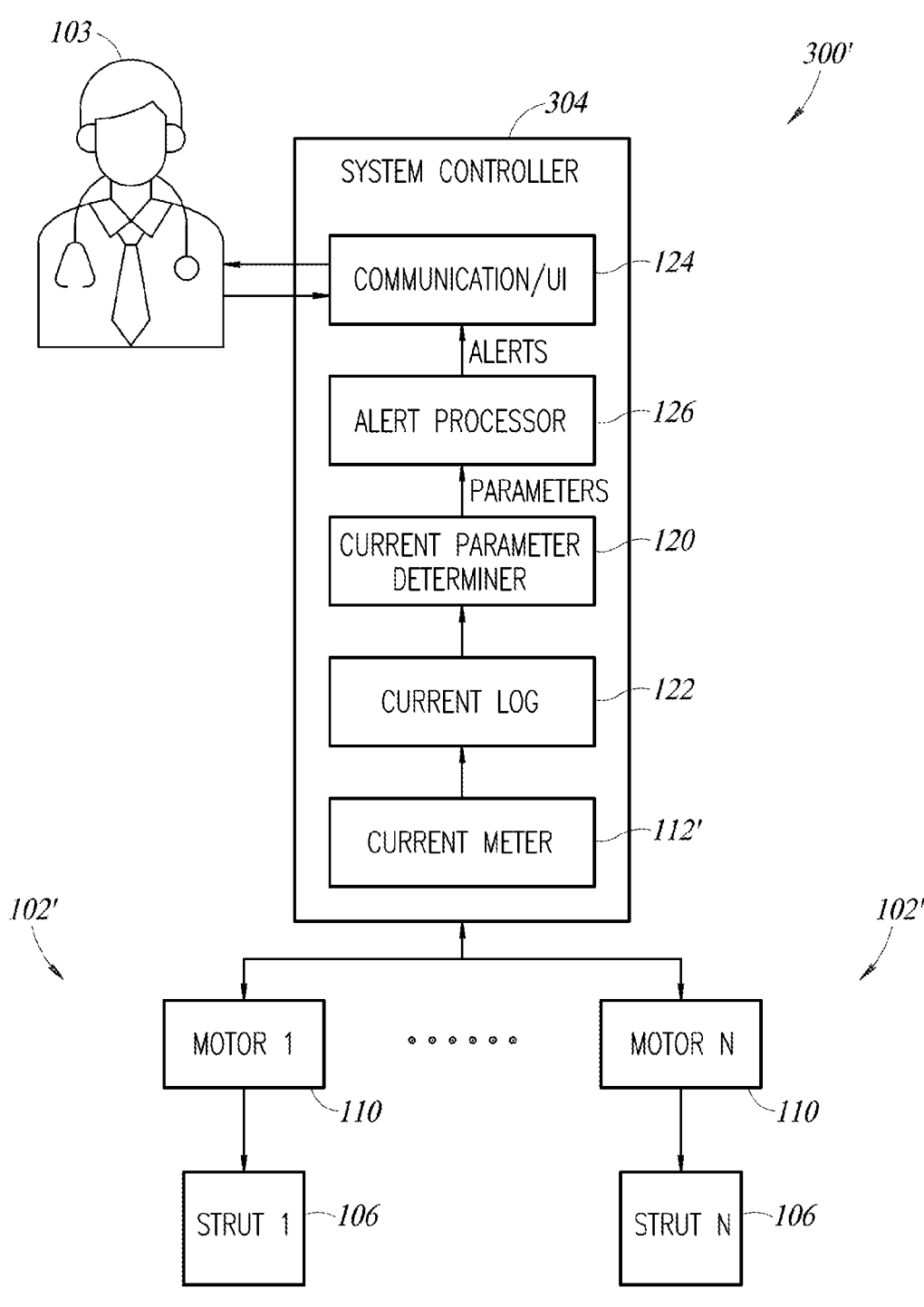

Reference is now made to FIG. 4B, which illustrates an alternative alert system, labeled 300', for a bone fixation device which has only a single current meter, here labeled 112', to be shared among strut units, here labeled 102', where each strut unit comprises its motor 110. In this embodiment, system controller 304 may separately activate each motor 110 according to the treatment plan, so that current meter 112' measures only the motor current used to activate the currently active strut unit 102'. System controller 304 may indicate to current log 122 which strut unit 102' is the currently active one, so that current log 122 may store the measured current per currently active strut unit 102'.

Current parameter determiner 120, alert processor 126 and communication unit 124 may operate as described in the embodiment of FIG. 4A.

Figure 5:
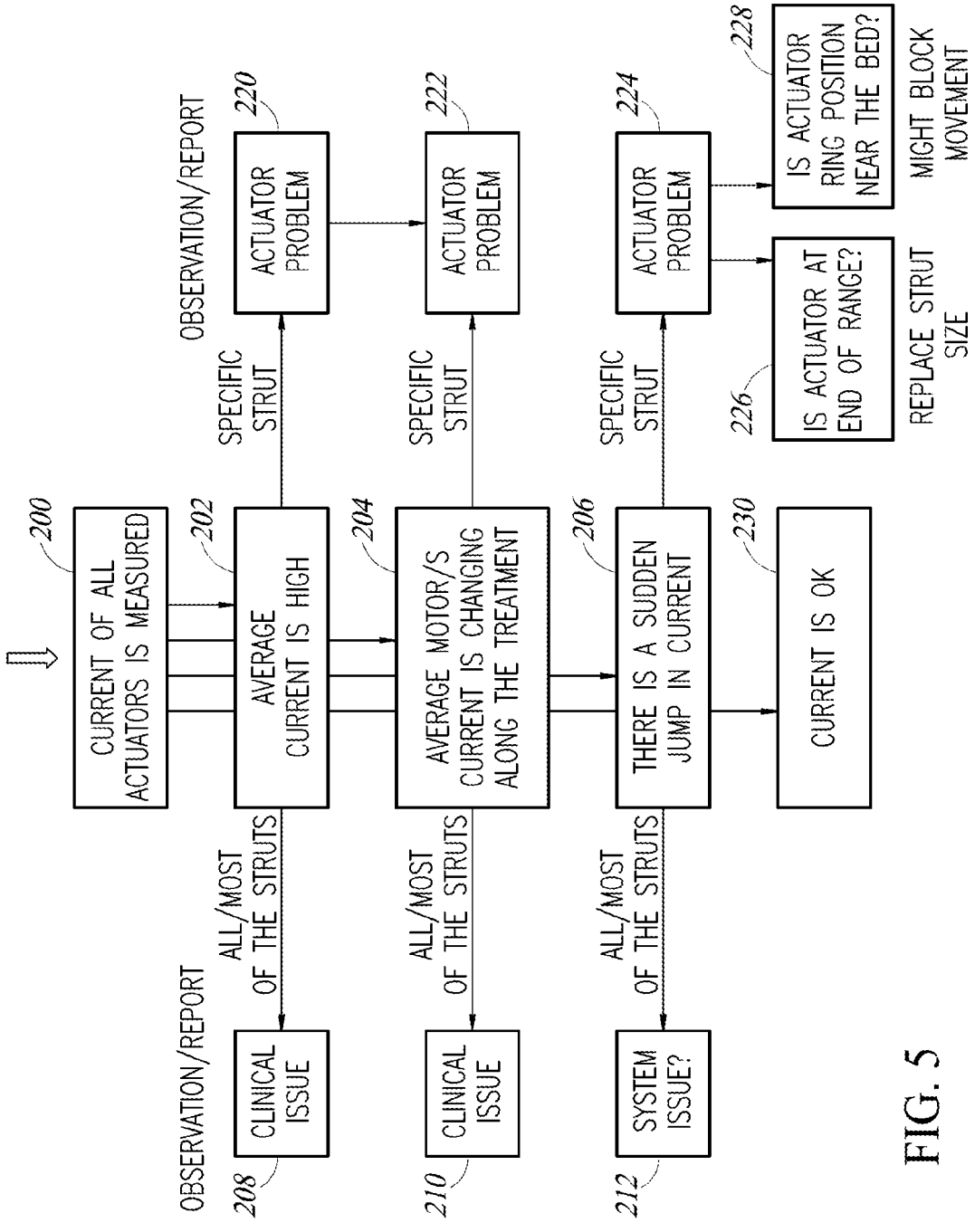
FIG. 5 is a flow chart illustration of the operation of the alert systems of FIGS. 4A and 4B.

Reference is now made to FIG. 5, which illustrates, in flow chart format, the operation of alert processor 126 when reviewing the data in current log 122 to determine if there is a problem and if there is a problem, whether it is a clinical problem or a system problem.

Initially, in step 200, current log 122 may receive the values of the current from the active current meter 112 or 112'. At some predefined time, whether once a new current data is received, once a second, once a minute once a day or on some other schedule, current parameter determiner 120 may determine the average current (step 202), the average motor current (step 204) and whether or not there was the peak current (step 206), for each strut unit 102/102'. If all of these values are within range, then there is no failure to be handled, as checked by alert processor 126 in step 230.

As can be seen, if a motor of a single strut 106 has an out-of-range average current, as checked in step 202, or if a motor of a single strut 106 has an average current which changes along the treatment, as checked in step 204, or if a motor of a single strut 106 has a sudden jump in its current, as checked in step 206, current parameter determiner 120 may determine, in steps 220, 222 and 224, respectively, that there is probably a problem with its strut. A sudden jump in current may be defined as a change (e.g., an abrupt change) in current, as checked in step 206, over a predetermined period of time that is greater than a predetermined current amount. If step 224 is positive, alert processor 126 may check if the relevant strut 106 is at the end of its predetermined travel limits (step 226) in which case, strut unit 102/102' may need to be replaced. To do so, alert processor 126 may ask system controller 304 to compare the current axial location of the relevant strut 102/102' to its predefined travel limits or may instruct communication unit 124 to ask the caregiver to check the relevant strut 102/102'. Alert processor 126 may also ask the caregiver to check if the relevant strut unit 102/102' or ring 14 is near the bed or an obstacle, as that might block movement of the fixation device of which strut units 102/102' form a part.

However, if the motors of all or most of the struts have the same issues, it is likely either a clinical issue (e.g., a clinical situation) or a system issue (e.g., system problem). FIG. 5 shows that if a motor of a single strut has an out-of-range average current, as checked by alert processor 126 in step 202, or if a motor of a single strut has an average current which changes along the treatment, as checked in step 204, alert processor 126 may determine, in steps 208 and 210, respectively, that there is probably a clinical issue that needs to be addressed.

If motors of multiple struts have a sudden jump in their current, as checked in step 206, alert processor 126 may determine, in step 212 that there is probably a system issue that needs to be addressed.

It will be appreciated that, via the review of the output of current meter(s) 112, device 300 or 300' may enable the physician, care giver or patient to identify problems with the activation of the fixation device, whether they be system problems or clinical problems, and to address them accordingly.

It will further be appreciated that the review of the output of current meter(s) 112 may enable device 300 or 300' to determine if a strut swap was not done (e.g., performed) or was forgotten and to provide an appropriate alert.

Figure 6:
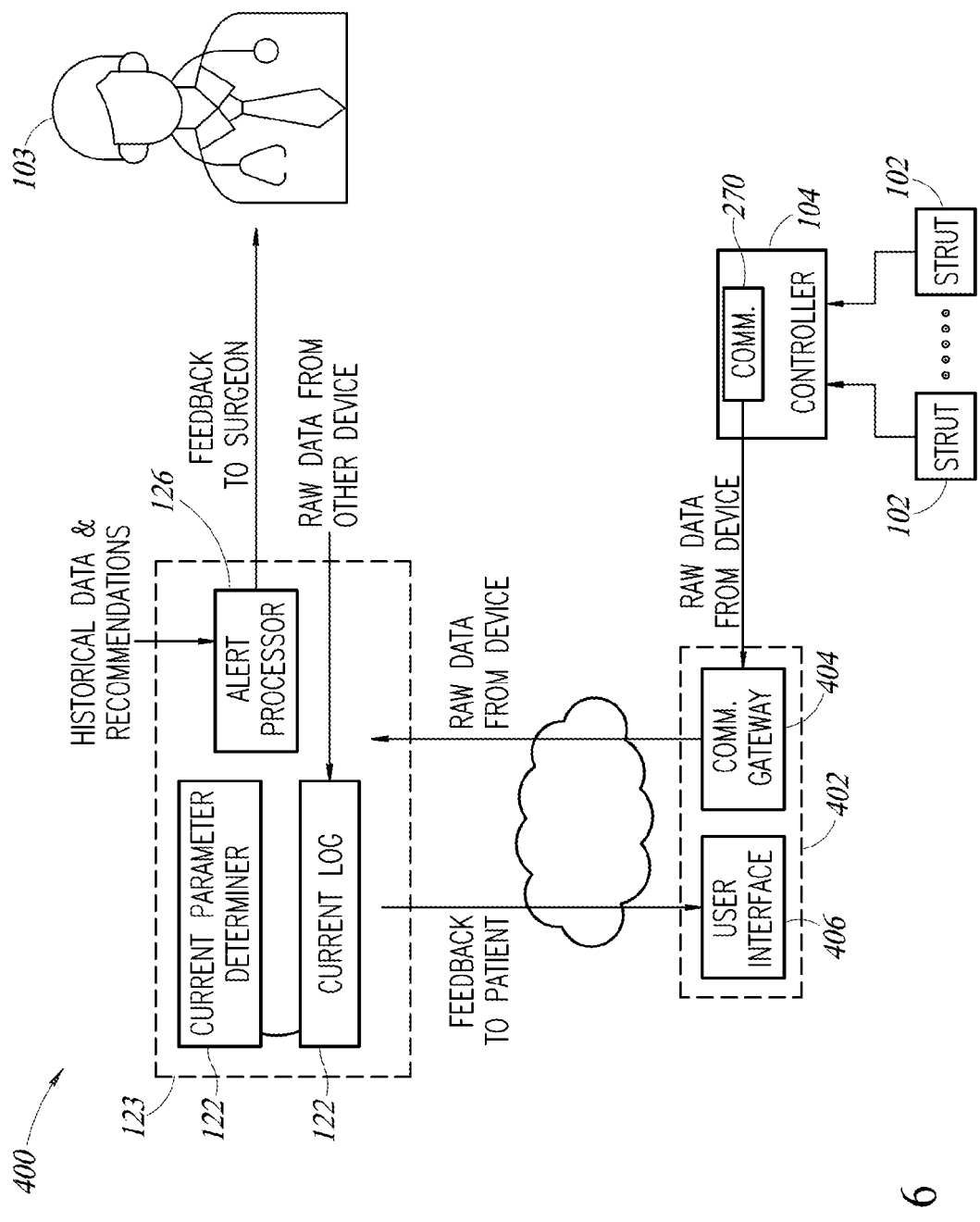
FIG. 6 is a schematic illustration of an alert system for one or more automated, motorized bone fixation devices.

Reference is now made to FIG. 6, which illustrates an alert system 400 for one or more automated, motorized bone fixation devices 100. In this embodiment, an alert unit 123, comprising current log 122, current parameter determiner 120 and alert processor 126, may be located remotely, such as on a separate server connected to a wide area network (WAN) such as the Internet, and may receive current data from multiple bone fixation devices 100.

Figure 2A:
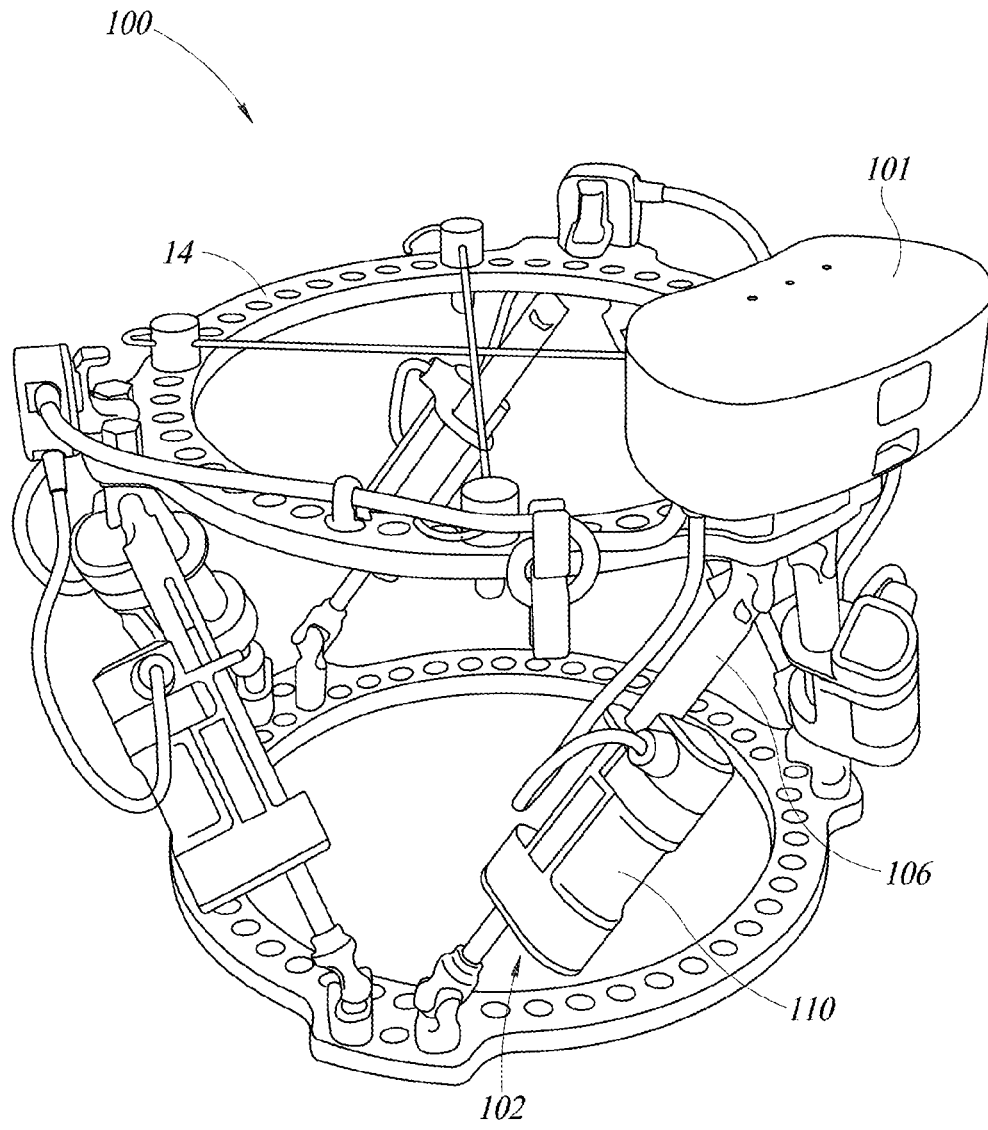
FIGS. 2A and 2B are schematic illustrations of an exemplary motorized external bone fixation device and its control unit, respectively.
Figure 2B:
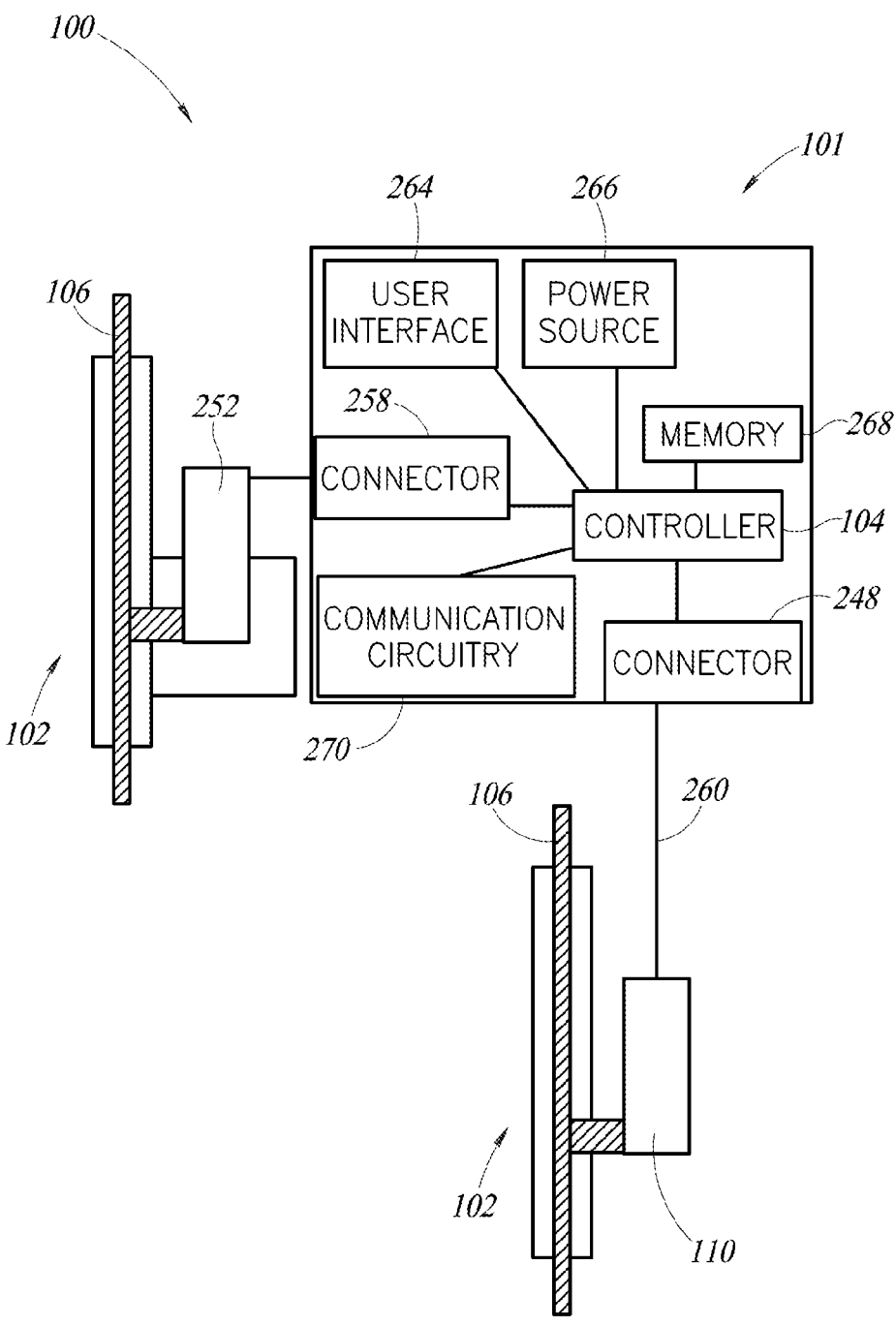

As discussed with respect to FIG. 2B, each bone fixation device 100 may comprise system controller 104 which may communicate, via communication circuitry 270, to an external device. In system 400 of FIG. 6, the external device may be a smartphone 402 of the patient or of his/her caregiver and may comprise a communication gateway 404 and a user interface 406.

Each communication gateway 404 may be wirelessly connected to communication circuitry 270 of its associated bone fixation device 100 and may be wirelessly connected to alert unit 123 via any standard internet connection. Each communication gateway 404 may be configured to receive the raw current data from its associated system controller 104 and to transmit the data, immediately or at periodic intervals, to current log 122 of alert unit 123. Current log 122 may associate the data with the relevant strut of the relevant device 100.

Current parameter determiner 122 and alert processor 126 may operate as described hereinabove. Alert processor 126 may provide feedback to physician or surgeon 103 as well as back to user interface 406 of smartphone 402, thereby providing feedback to the patient or caregiver as well.

Alert unit 123 may also receive historical data from other bone fixation devices 100 and may review such data to provide recommendations for treatments.

It will be appreciated that alert unit 123 may provide surgeons 103 with real-time or close to real-time data about how their patients are faring with their bone fixation devices 100, enabling the surgeons 103 to provide relatively quick responses when issues arise.

It will be appreciated that the embodiment of FIGS. 4A and 4B utilizes electrical current as an indicator for torque on motors 110 and utilizes torque or current as an indicator for a clinical or a system condition, since in brushed motors, there is a direct and linear correlation between the current and the torque.

Figure 7A:
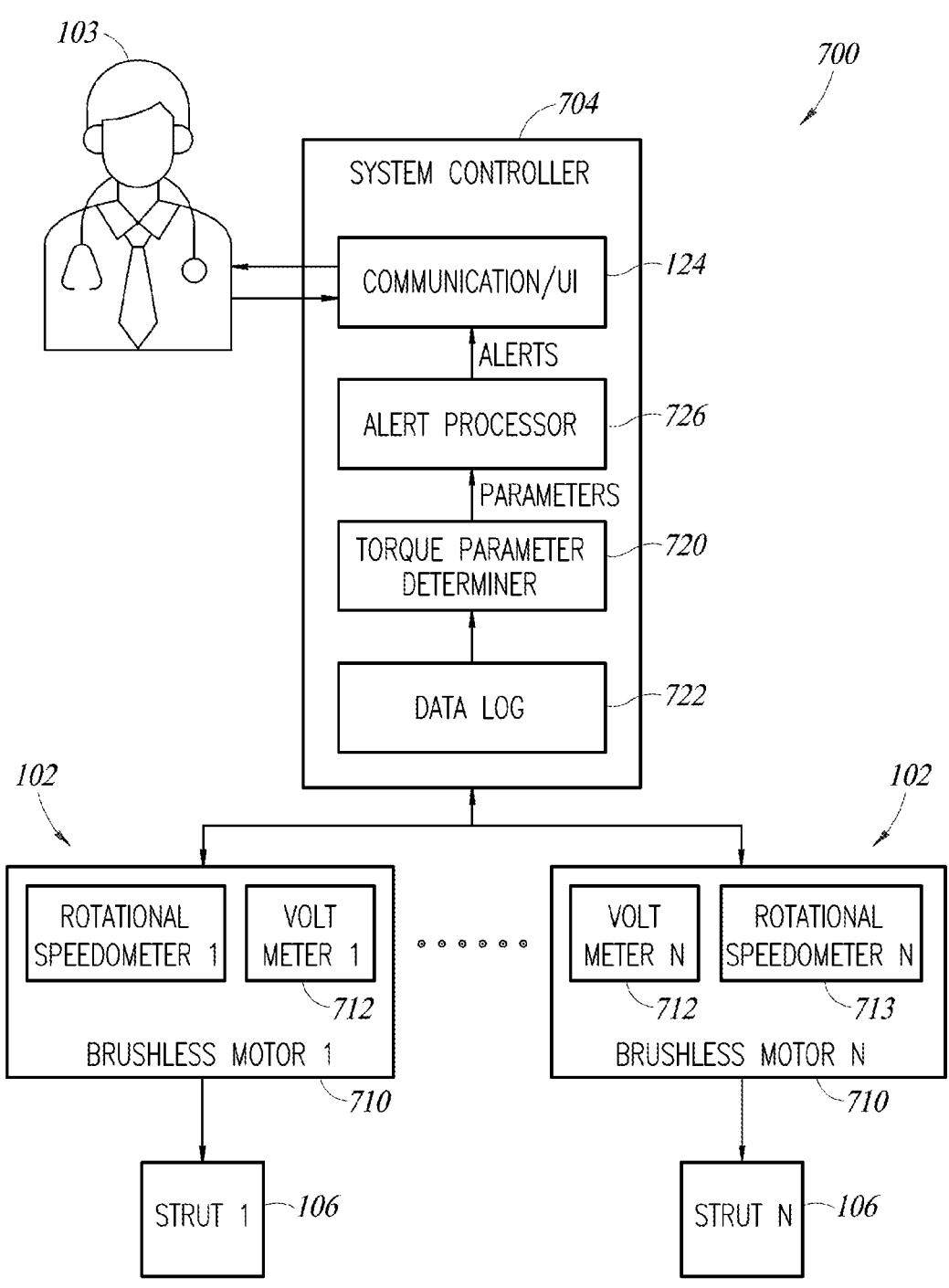
FIG. 7A is a schematic illustration of a further embodiment of an alert system for an automated, motorized bone fixation device, constructed and operative in accordance with a further preferred embodiment of the present disclosure.
Figure 7B:
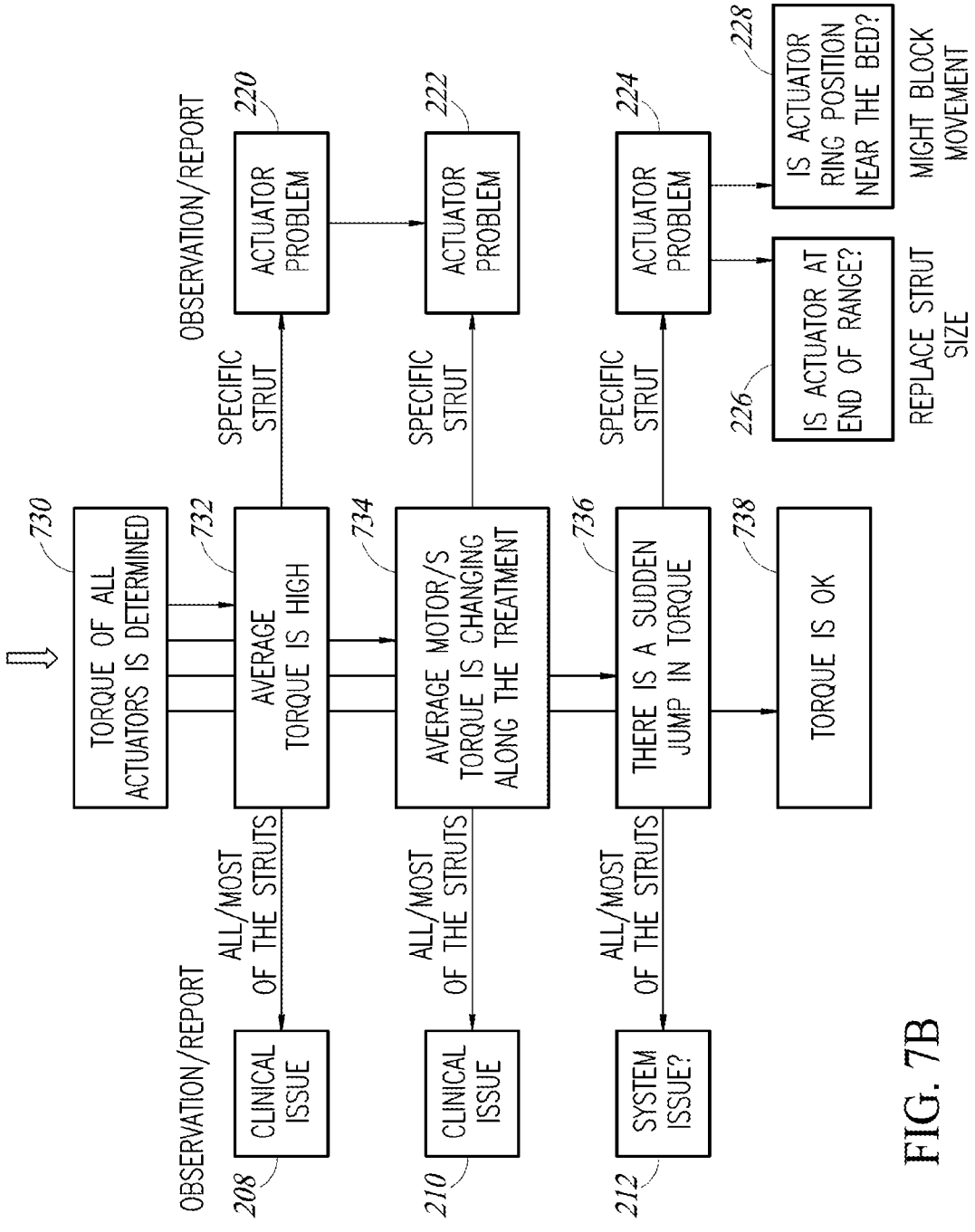
FIG. 7B is a flow chart illustration of the operation of the alert system of FIG. 7A.

It can be appreciated that other measurements may be used to indicate torque on a motor, depending on the type of motor used. This is shown in FIGS. 7A and 7B, to which reference is now made, which show a further automated motorized bone fixation device, here labeled 700, having brushless motors 710.

In a brushless DC motor, the relationship between the applied voltage (V) and the load torque determines the rotational speed, in accordance with the following relationship:

$$\text{mechanical power} = f(V) = \text{torque} * \text{rotational speed} \quad (1)$$

As a result, by measuring voltage and rotational speed, the torque or load on the brushless motors 710, such as produced by the growth or lack thereof of the leg, may be determined.

As in the embodiment of FIGS. 4A and 4B, device 700 comprises at least two strut units, here labeled 702, and a system controller, here labeled 704. Each strut unit 702 comprises a strut 106 and a brushless electric motor 710. Each brushless electric motor 710 may be connected to a voltmeter 712, which may measure the voltage applied by its motor 710, and to a rotational speedometer 713, such as a rotational encoder, which may measure the rotational speed of its motor 710.

System controller 704 may comprise a data log 722, in which each meter 712 and 713 may store the voltage and rotational speed values it has sensed, a torque parameter determiner 720, an alert processor 726 and a communication unit 124. Torque parameter determiner 720 may determine the torque currently being applied by each motor 710, such as by using equation 1, and may then determine various parameters of the torque, such as the average torque (for a given period of time), the peak torque, change in the average torque etc. Alert processor 726 may generate alerts if any of these values, or a combination of these values, or a combination of these values with those of another sensor, are outside of a predefined range. Torque parameter determiner 720 may also regularly report on the activations of strut units 102 to physician 103 and may transmit alerts as they occur.

FIG. 7B is similar to FIG. 5 but illustrates the operation of alert processor 726 when reviewing the data in data log 722. In FIG. 7B, the data being reviewed are the parameters of the determined torque rather than of the measured current and thus, steps 200, 202, 204, 206 and 230 have been relabeled as steps 730, 732, 734, 736 and 738.

It will be appreciated that, the embodiments herein described determine torque in some way (either by measuring current in the brushed motor case or by calculating it from the measured voltage and rotational speed in the brushless motor case) and utilize the results as indication of the clinical or system state.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a hardware controller, mobile computing devices, smart appliances, or similar electronic computing devices that manipulate and/or transform data within the computing system's registers and/or memories into other data within the computing system's memories, registers or other such information storage, transmission or display devices.

Embodiments of the present disclosure may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general-purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general-purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present disclosure are not described with reference to any particular programming language. It will be appreciated if a variety of programming languages may be used to implement the teachings of the disclosure as described herein.

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An adjustable bone fixation device for moving a bone, the adjustable bone fixation device comprising:
    at least two strut units, each strut unit of the at least two strut units comprising a motor to move a strut;
    at least one meter to measure a signal generated by the motor during a movement of the respective strut, said signal useful in determining a torque or a current of said motor;
    a system controller to activate at least two motors of the at least two strut units and to determine said torque or said current of the at least two motors; and
    an alert processor to identify if said determined torque or said determined current indicates a clinical situation of the bone or a system issue and to provide an alert accordingly, wherein the alert processor determines if a strut swap was not done or was forgotten and provides an appropriate alert.

2. The adjustable bone fixation device of claim 1, wherein said motor is a brushed motor and said at least one meter is a current meter.

3. The adjustable bone fixation device of claim 1, wherein said motor is a brushless motor, wherein said at least one meter is a voltmeter and a rotational speedometer.

4. The adjustable bone fixation device of claim 1, wherein the alert processor identifies a problem when at least one parameter of the determined torque or the determined current is out of a predetermined range for the at least one parameter.

5. The adjustable bone fixation device of claim 1, wherein the alert processor determines that a single strut unit of the at least two strut units has a problem if a motor of the single strut unit has an out-of-range value for a parameter of the determined torque or the determined current.

6. The adjustable bone fixation device of claim 1, wherein the alert processor determines said clinical situation if a majority of said motors have an out-of-range value for a parameter of their respective determined torques or determined currents.

7. The adjustable bone fixation device of claim 1, wherein the alert processor determines that a single strut unit of the at least two strut units has a problem if a motor of the single strut unit has a sudden jump in a value for a parameter of the determined torque or the determined current.

8. The adjustable bone fixation device of claim 7, wherein if the alert processor classifies the problem as an end of travel problem, the alert processor instructs the system controller to compare a current axial location of the single strut unit with a predefined travel limit for the single strut unit.

9. The adjustable bone fixation device of claim 1, wherein the alert processor determines that a single strut unit has a problem if the motor of the single strut unit has a continuous elevation of a value for a parameter of the determined torque during a treatment period.

10. The adjustable bone fixation device of claim 1, wherein the alert processor identifies the clinical situation if a majority of said motors have a continuous elevation of a value for a parameter of the determined torques or the determined currents during a treatment period.

11. The adjustable bone fixation device of claim 1, wherein said alert processor is located remotely to said adjustable bone fixation device.

12. The adjustable bone fixation device of claim 11, wherein said system controller comprises communication circuitry to communicate to an external device which communicates with the alert processor.

13. The adjustable bone fixation device of claim 12, wherein the external device is a smartphone of a patient or a caregiver.

14. A method for an adjustable bone fixation device for moving a bone, the adjustable bone fixation device having at least two strut units, each strut unit of the at least two strut units comprising a motor to move a strut, the method comprising:

activating at least two motors of the at least two strut units;

measuring signals generated by said at least two activated motors, said signals useful in determining torques or currents of said at least two motors; and identifying if the determined torques or currents indicate a clinical situation of the bone or a system issue and alerting accordingly, wherein identifying if the determined torques or currents indicate the clinical situation comprises determining if a strut swap was not done or was forgotten and providing an appropriate alert.

15. The method of claim 14, wherein said at least two activated motors are brushed motors and said signals are current signals.

16. The method of claim 14, wherein said at least two activated motors are brushless motors, and wherein said signals are voltage signals or rotational speed signals.

17. The method of claim 14, wherein identifying if the determined torques or currents indicate the clinical situation comprises reviewing said determined torque or said determined current to determine when at least one parameter of said determined torque or said determined current is out of a predetermined range for the at least one parameter.

18. The method of claim 14, wherein identifying comprises determining that a single strut unit of the at least two strut units has a problem if a motor of the single strut unit has an out-of-range value for a parameter of the determined torque.

19. The method of claim 14, wherein identifying if the determined torques or currents indicate the clinical situation comprises determining said clinical situation if a majority of said motors have an out-of-range value for a parameter of their determined torques or determined currents.

20. The method of claim 14, wherein identifying if the determined torques or currents indicate the clinical situation comprises determining that a single strut unit has a problem if a motor of the single strut unit has a sudden jump in a value for a parameter of the determined torque or the determined current.

21. The method of claim 20, wherein if the problem is classified as an end of travel problem, comparing a current axial location of the single strut unit with a predefined travel limit for the single strut unit.

22. The method of claim 14, wherein identifying if the determined torques or currents indicate the clinical situation comprises determining that a single strut unit has a problem if the motor of the single strut unit has a continuous elevation of a value for a parameter of the determined torque or the determined current during a treatment period.

23. The method of claim 14, wherein identifying if the determined torques or currents indicate the clinical situation comprises identifying the clinical situation if a majority of said motors have a continuous elevation of a value for a parameter of the determined torques or the determined currents during a treatment period.

* * * * *